United States Patent [19]

Hartman

[11] Patent Number: 4,654,313
[45] Date of Patent: Mar. 31, 1987

[54] METHODS FOR THE DETERMINATION OF BRAIN ANTIGENS

[75] Inventor: Boyd K. Hartman, St. Louis, Mo.

[73] Assignee: The Washington University, St. Louis, Mo.

[21] Appl. No.: 555,061

[22] Filed: Nov. 25, 1983

[51] Int. Cl.$^4$ .......................................... G01N 33/536
[52] U.S. Cl. .................................... 436/542; 436/804; 436/811; 436/815; 436/825
[58] Field of Search ............... 436/542, 804, 811, 815, 436/825

[56] References Cited

U.S. PATENT DOCUMENTS

| | | | |
|---|---|---|---|
| 4,136,160 | 1/1979 | Cohen | 436/804 |
| 4,311,686 | 1/1982 | Angers et al. | 436/545 |
| 4,399,217 | 8/1983 | Holmquist et al. | 435/7 |

OTHER PUBLICATIONS

Palfreyman et al., Clin. Chim. Acta, 82(1978), 259–70.
Steinberg et al., J. Neurochem., 43(1), 1984, 19–24.
Ghandour et al., J. Neurochem., 36(1), 1981, 195–200.
Excerpt from Principles of Competative Protein-Binding Assays, Ed. Odell et al., Lippincott, Philadelphia, 1971, pp. 331–332.

*Primary Examiner*—Christine M. Nucker
*Attorney, Agent, or Firm*—Senniger, Powers, Leavitt and Roedel

[57] ABSTRACT

A radioimmunoassay method for the determination of brain antigens or protein such as S-100 responsible for neurological disorders is disclosed. The method involves preparing a standard blood plasma or serum formulation containing substantially none of the protein being assayed and approximately the average degree of non-specific competitive binding found in the unknown blood sample and mixing known quantities of the protein being assayed with the standard blood formulation to provide a reference standard. The unknown blood sample is then mixed with a radioactively labeled sample of the protein being assayed and an antibody capable of immunoreactivity with the protein, the mixture is incubated, the antibody bound protein is separated from the unbound protein and the relative amounts of antibody bound and unbound protein are determined. Then, the antibody mixing, incubation and separation steps are separately repeated with an unknown blood sample from which the protein being assayed has been substantially removed to provide information for the calculation of a corrected protein level. The amount of the protein being assayed is then determined from the reference standard and the separate determinations made with the unknown blood samples both with and without the protein being assayed present therein.

6 Claims, 3 Drawing Figures

A. NON-NEUROLOGICAL CONTROLS (NON-LIFE THREATENING DISORDERS)

B. NON-NEUROLOGICAL CONTROLS (LIFE-THREATENING DISORDERS)

C. ACUTE NEUROLOGICAL DISORDERS (RANDOM SELECTION)

METHODS FOR THE DETERMINATION OF BRAIN ANTIGENS

BACKGROUND OF THE INVENTION

This invention relates to radioimmunoassay methods and more particularly to radioimmunoassay methods for the in vitro determination from an unknown test blood sample of a normal soluble endogenous cytoplasmic protein, such as S-100, released into the blood in the course of neurological diseases and which is susceptible to separation from other proteins simultaneously released into the blood.

As is known, the nervous system contains a number of proteins unique to its various cellular elements. The cellular disruption of nervous tissue, by any pathogenic process or by neurological diseases, results in the release of normal soluble endogeneous cytoplasmic proteins into the cerebral extracellular fluid and ultimately to other body fluids including the cerebrospinal fluid (CSF) and blood (serum and plasma). Representative small molecular weight, soluble, proteins of this type normally present in reasonably high concentrations have been isolated for glial cells (S-100), neurons (14-3-2) and myelin (PLP). Following disruption of cell membranes, these proteins are released into the extracellular fluid in accordance with a time course and in quantities relative to the pathogenesis of the disease process. These proteins diffuse into the CSF and then the blood. The progression of the disease process is reflected by the blood plasma or serum levels of one or more of these protein antigens or markers. These protein antigens have the advantage of being stable and specific, not only for the brain, but for the cellular components in the brain. If the relative release of the various nervous system protein antigens could be followed, it would make it possible to deduce the kind of destructive process occurring in the course of neurological diseases. Information of this type would permit the diagnosis, evaluation of severity and rate of progression of neurological diseases that result in cellular damage.

A need has existed, therefore, for practical means for the in vitro determination from an unknown test blood sample of a normal soluble endogenous cytoplasmic protein, such as S-100, released into the blood in the course of neurological diseases. Such a determination would be a great aid to the clinician in more precisely evaluating the extent of actual damage in strokes or other neurological disorders, especially early in the course when the clinical picture is frequently obscured by neurological disfunction resulting from inflammation and edema.

SUMMARY OF THE INVENTION

Among the several objects of the invention may be noted the provision of a radioimmunoassay method for the in vitro determination from an unknown test blood sample of a normal soluble endogeneous cytoplasmic protein released into the blood in the course of neurological diseases which provides the clinician with useful information as to the diagnosis, evaluation of severity and rate of progression of neurological diseases; the provision of such a method which possesses the necessary sensitivity and reliability to yield useful clinical information; the provision of a method of this type which is advantageously non-invasive and virtually without risk to the patient; and the provision of such a method which is relatively inexpensive and can be carried out in clinical laboratories having the capacity to do conventional radioimmunoassays. Other objects and features will be in part apparent and in part pointed out hereinafter.

Briefly, the invention is directed to a radioimmunoassay method for the in vitro determination from an unknown test blood sample of a normal soluble endogenous cytoplasmic protein released into the blood in the course of neurological diseases and which is susceptible to separation from other proteins simultaneously released into the blood which method comprises the steps of: (a) preparing a standard blood formulation containing substantially none of the protein being assayed and approximately the average degree of non-specific competitive binding found in the unknown test blood sample; (b) mixing known quantities of the protein being assayed in purified form with the standard blood formulation to form a reference standard; (c) mixing the unknown test blood sample with a radioactively labeled sample of the protein being assayed and an antibody capable of immunoreactivity with the said protein; (d) incubating the last resultant mixture to produce antibody bound radioactively labeled protein and unbound radioactively labeled protein; (e) separating the antibody bound protein from the unbound protein; (f) determining the relative amounts of antibody bound radioactively labeled protein and unbound radioactively labeled protein; (g) separately repeating steps (c), (d), (e) and (f) with an unknown test blood sample from which the protein being assayed has been substantially removed; and (h) determining the amount of the protein being assayed from the reference standard and the determinations made in steps (f) and (g).

DESCRIPTION OF THE PREFERRED EMBODIMENTS

In accordance with the present invention, it has now been found that a non-invasive and relatively inexpensive radioimmunoassay method for the in vitro determination from an unknown test blood sample of a normal soluble endogenous cytoplasmic protein released into the blood in the course of neurological diseases and which is susceptible to separation from other proteins simultaneously released into the blood may be achieved by carrying out the steps described below.

In the novel radioimmunoassay method of the invention, there is first prepared a standard blood formulation containing substantially none of the protein being assayed and approximately the average degree of nonspecific competitive binding found in the unknown test blood sample. Next, there is mixed known quantities of the protein being assayed in purified form with the above-noted standard blood formulation to provide a reference standard. Then, the unknown test blood sample is mixed with a radioactively labeled sample of the protein being assayed and an antibody capable of immunoreactivity with the protein being assayed. This is followed by incubation of the last resultant mixture to produce antibody bound protein and unbound protein, separation of the antibody bound protein from the unbound protein, and a determination of the relative amounts of antibody bound radioactively labeled protein and unbound radioactively labeled protein. The last four above-described steps are then repeated with an unknown test blood sample from which the protein being assayed has been substantially removed and, finally, a determination is made of the amount of the protein being assayed from the reference standard and the determination made in several of the above-described steps, namely, the steps of determining the relative amounts of antibody bound radioactively labeled protein and unbound radioactively labeled protein and the repeated steps as aforesaid.

While the methods of the invention are generally applicable to various blood proteins, as will be made clear hereinafter, the following description is specific to the blood protein designated S-100, a glial marker which is exemplary of the blood proteins as to which the invention may be utilized and has been found practical. It will thus be understood that the radioimmunoassay methods may be adapted for the determination of other normal soluble endogenous cytoplasmic proteins such as 14-3-2 protein, a neuronal marker, and the myelin markers basic protein (BP) and proteolipid protein (PLP).

As stated, following disruption of cell membranes by any pathogenic process, these proteins are released into the extracellular fluid in accordance with a time course and in quantities relative to the pathogenesis of the disease process. These proteins diffuse into the CSF and then the blood. The progression of the disease process is reflected by the plasma levels of one or more of these protein antigens. The measurement of serum enzymes is carried out as an aid in the diagnosis of peripheral disease, but the protein antigens have the advantage of being more stable and specific, not only for the brain, but for the cellular components in the brain. By following the relative release of the various nervous system protein antigens, it becomes possible to deduce the kind of destructive process involved. The type of information derived through the practice of the present invention is useful in more precisely evaluating the extent of actual damage in stroke or other neurological disorders, especially early in the course when the clinical picture is frequently obscured by neurological disfunction that results from inflammation and edema. The radioimmunoassay of the invention is especially useful for detecting diffuse disorders which are frequently CAT scan negative, for following the course of a disorder and for evaluating the effect of treatment independently of the clinical picture. This last feature is of particular importance because the resolution of clinical signs and symptoms usually lag behind the events within the brain, sometimes leading to erroneous conclusions regarding the effectiveness of ineffectiveness of a particular treatment. Moreover, the assay of the present invention has the significant advantage of being non-invasive, virtually without risk to the patient and relatively inexpensive since it can be readily carried out by any clinical laboratory with the capacity to do radioimmunoassays.

The protein S-100 is one of the most intensively studied nervous system specific proteins and serves as a prototype for describing the present invention. S-100 is a relatively small (molecular weight=21,000–24,000) soluble acidic protein. It is present in high concentration in brain (>150 g/gm tissue in human brain, Moore, B. W., Acidic Proteins, Handbook of Neurochemistry, 1:93–99, 1969). S-100 is present in the glial elements (Hyden et al., A glial protein specific for the nervous system, Proc. Nat. Acad. Sci., 55:354–358, 1966; Benda et al., Differentiated rat glial cell strain in tissue culture, Science, 161:370–371, 1968; Perez and Moore, Wallerian degeneration in rabbit tibial nerve: changes in amounts of the S-100 protein, J. Neurochem., 15:971–977, 1968; Perez et al., Wallerian degeneration in rabbit optic nerve: cellular localization in the central nervous system of the S-100 and 14-3-2 proteins, J. Neurochem., 17:511–519, 1970; and Cicero et al., The cellular localization of the two brain specific proteins, S-100 and 14-3-2, Brain Research, 18:25–34, 1970) including human glial tumors. The protein has remarkably broad species crossreactivity (Moore, B. W., Brain-specific proteins: S-100 protein, 14-3-2 protein and glial fibrillary protein. Advances in Neurochemistry, 1:137–175, 1975 and Levine and Moore, Structural relatedness of a vertebrate brain acidic protein as measured immunochemically, Neurosci. Res. Prog. Bull, 3:18–22, 1965) indicating a high degree of phylogenetic preservation. The protein is present in brain in at least three distinguishable molecular forms. The antiserum or antibody utilized in the present invention recognizes all of them.

Preliminary data was collected indicating the feasibility of using S-100 protein as a marker for destructive neurological disease. First, radioactively tagged S-100 stereotoxically injected into parietal cortex of rabbits appeared in the CSF within fifteen minutes of injection. Peak CSF levels occurred at 2 hours and were essentially cleared within 6 hours. Radioactive S-100 was measurable in serum within one hour and reached at its maximum at six hours. This indicated that no absolute brain-CSF or CSF-blood barriers were present. Second, destructive experimental intracerebral lesions of variable sizes were made in rabbits. These lesions resulted in the appearance of immunoreactive S-100 (measured by RIA) in CSF and plasma with levels proportional to the size of the lesion indicating that S-100 can gain access to blood in a form recognizable by its antibody.

In accordance with the invention, I have found that an accurate, sensitive, reproducible and clinically useful radioimmunoassay method for the determination of a normal soluble endogenous cytoplasmic protein, such as S-100, released into the blood in the course of neurological diseases is achieved by carrying out the following series of steps. First, a standard blood formulation is prepared which contains substantially no S-100 and which contains approximately the average degree of non-specific binding interference found in the unknown test blood sample (e.g. patient plasma). To prepare this standard formulation, the S-100 is removed as described hereinafter without also removing the positively charged blood or plasma proteins responsible for non-specific competition. The requirement that the standard formulation contain approximately the average degree of non-specific binding found in the unknown test blood sample is met by pooling a relatively large number (e.g.

250) of different randomly collected blood or plasma samples. A standard or reference curve is then constructed by mixing known quantities of S-100 in purified form with the standard blood formulation (see FIG. 1).

Next the unknown test blood sample is mixed with a radioactively labeled sample of S-100 and an antibody capable of immunoreactivity with S-100, the mixture is incubated to produce antibody bound S-100 and unbound S-100, the antibody bound S-100 is separated from the unbound S-100 and the relative amounts of antibody bound radioactively labeled S-100 and unbound radioactively labeled S-100 are determined to provide a measurement of the counts per minute bound to the specific antibody by the unknown serum or plasma sample as $CPM_u$. This last series of steps is then separately repeated with an unknown test blood sample from which S-100 has been substantially removed without removing the proteins responsible for non-specific binding to provide a measurement of the counts per minute bound to the specific antibody by the unknown blood or plasma sample with no S-100 therein (referred to herein as Max $Blank_u$). This last measurement is important in the practice of the invention and permits an accurate evaluation of the degree to which non-specific competitive binding is interfering with the interaction between radioactively labeled S-100 and the antibody in that particular sample as compared to the same property in the standard blood plasma formulation. There is a definable relationship between the degree to which the non-specific binding proteins interfere with antibody binding to radioactively labeled S-100 and their effect on endogenous S-100 binding in the same blood or plasma sample. Thus, through the assay method of my invention, it is possible to accurately assess the concentration of an antigen such as S-100 in the presence of variable and unknown quantities of non-specific binding interference.

The present invention effectively overcomes the problem presented because S-100 is highly negatively charged and has a non-specific binding affinity for positively charged plasma proteins (mostly gamma globulins). Each blood sample or plasma is somewhat different in regard to the quantity of such interfering proteins. Though the strength of this affinity is small compared to that of the specific antibody, because of the comparatively large quantities of globulins in blood or plasma, the net effect on the competitive binding curve is significant. The result is a 20% decrease in the maximum binding of radioactively labeled (using $^{125}I$ or other radioisotope) S-100 under assay conditions in the presence of plasma compared to optimal assay conditions in buffer. The use of pooled human sera or plasma in the media for preparing the standard curve as previously described does not completely correct for this problem because it only produces a medium with an average amount of inhibitory activity. The greater an individual sample differs from this "average", the greater will be the overestimation or underestimation of its S-100 level. Accordingly, in the absence of the second determination or measurement made in the practice of the present invention with an unknown blood or plasma sample from which S-100 has been substantially removed, the clinical usefulness of the results in the evaluation of individual patients is markedly reduced by reason of this problem even though it does not greatly affect statistical analysis. Thus, the aforementioned problem is overcome through the present invention by evaluating the degree of binding interference on each blood sample and using this information to calculate a corrected S-100 level as brought out more fully hereinafter. The assay of the invention hence provides a measured level of S-100 or other protein which is reproducible (even when frozen samples are retested after months), sufficiently accurate and sensitive to be clinically useful when utilized to assay S-100 samples prepared with known amounts of authentic human protein and sufficiently reliable to correctly estimate known S-100 levels in blood or plasma samples with greatly different quantities of interfering proteins.

With the radioimmunoassay method of the invention, the range for determination of S-100 is 0 to 20.0 ng/ml. The reproducibility is $\pm 10\%$ (SD) in the optimal (SD) assay range of 2 to 6 ng/ml where most neurological patients fall and $\pm 20\%$ at the extremes of the curve. False negatives are completely eliminated at values >1.5 ng/ml when authentic S-100 was added to plasma samples as described.

As mentioned, the present invention may be employed for the determination of proteins other than S-100 such as 14-3-2, PLP and BP. Since BP is a positively charged protein, the separation step would entail the use of a negatively charged material such as negatively charged Sephadex (e.g. CM Sephadex). The invention is not applicable to neutral proteins or highly charged proteins of a molecular weight approximating that of albumin.

The assay may be carried out using either plasma or serum as the blood sample.

Based upon the clinical studies conducted using the assay method of the invention, the following schedule may be used for clinically evaluating or interpreting S-100 levels.

| S-100 Level | Interpretation |
| --- | --- |
| 0.0 to 1.0 ng/ml | No active neurological disorder within 2 days of sample collection (65% of non-neurological controls fall in this category.) |
| 1.0 to 2.0 ng/ml | Not clinically informative without additional levels. Compatible with almost any neurological disorder which is in early or late stage of development or mild in degree (25% of non-neurological controls fall in this category). |
| 2.0 to 3.0 ng/ml | 90% Confidence: Active neurological disorder compatible with almost any active neurological disorder mild to moderate in severity. Most commonly there will be cerebral edema, small stroke, dementia, MS (slowly progressive), inflammation pseudotumor cerebri, etc. Disorders severe in degree may exhibit these levels early or late in their course (10% of non-neurological controls fall in this category). |
| 3.0 to 4.0 ng/ml | 98% Confidence: Active neurological disorder compatible with active MS, strokes, early tumors, dementia severe and progressive, encephalitis, pseudotumor. These patients will likely have significant residual deficit if levels are due to destructive process. (2% of non-neurological contols fall into this category). |
| 4.0 to 5.0 ng/ml | 100% Confidence: Active neuro- |

| S-100 Level | Interpretation |
| --- | --- |
| | logical disorder compatible with stroke, CNS tumor, encephalitis, head injury. These levels predict significant residual deficit. |
| 5.0 to 6.0 ng/ml | 100% Confidence: Active destructive neurological disorder compatible with stroke, brain tumor and encephalitis, but not compatible with MS, simple edema. Major residual deficit is likely. |
| 6.0 ng/ml or greater | 100% Confidence: Severe active destructive neurological disorder compatible with major stroked and brain tumors (especially glial). Major neurological deficit is predicted. |

For serially obtained samples, the following may be used for evaluating or interpreting S-100 levels:

Sustained Low Levels: No active disease.

Decreasing Levels: Good prognosis: Disease process exacerbating.

Sustained High Levels: Bad prognosis: Progressive destruction.

Changes in levels of:

1. Less than 0.5 ng/ml are not significant.
2. Between 0.5 and 1 ng/ml are significant.
3. Greater than 1 ng/ml are highly significant.

The following illustrates the practice of the invention.

PURIFICATION OF S-100 PROTEIN

The following flow diagram outlines the preparation of purified S-100 protein from the brain, either human or bovine, according to a modified method of Moore, B. W., A Soluble Protein characteristic of the Nervous System, Biochem. Biophys. Res. Commun., 19, 739, 1965.

The same procedure may be used for the preparation of purified 14-3-2 protein.

Bovine brain from the slaughterhouse is preferably used as the starting material although the S-100 protein may also be prepared by the same general method from other species, such as rabbit, hog, sheep, human and rat. Ake, T. et al. Purification and properties of S-100 protein from Porcine brain, J. Biochem. (Tokyo), 75, 11, 1974 and Uozumi, T. et al. Isolation, amino acid composition, and radioimmunoassay of human brain S-100 protein, Mayo Clin. Proc., 48, 50, 1973. The brains are stored frozen and thawed immediately before use. The extraction of S-100 proceeds better if the brains are frozen and thawed once before homogenization. The following description involves the use of 4 kg of whole beef brain.

The buffers employed during the preparation are as follows: "Buffer A" is 5 mM tri phosphate (5 mM in phosphate) pH 7.2 which is kept as a 0.5M stock solution and diluted 100 fold before use. "Buffer B" is 1M NaCl, 0.05M sodium phosphate, pH 7.2, and "Buffer C" is 1M NaCl, 0.05M soidum phosphate pH 6.2. The brains are homogenized in a Waring blender in 3 volumes of "Buffer A" to which 0.2 mM EDTA and 1 mM 2-mercaptoethanol have been added. All operations are carried out at 4° C. The homogenate is spun 4 hours at 10,000 RPM, the clear supernatant fluid is poured off, and the sediment is discarded. The above flow diagram illustrates the fractionation procedure.

The supernatant fluid ($S_1$) is brought to 40% saturation with ammonium sulfate by dissolving 243 g solid ammonium sulfate and 2.43 ml 1N NH$_4$OH in each liter of $S_1$. The suspension is spun 2 hours at 10,000 RPM and the clear supernatant fluid ($S_{40}$) is poured off. The $S_{40}$ solution is brought to 60% saturation by dissolving 132 g ammonium sulfate and 1.32 ml 1N NH$_4$OH in each liter of $S_{40}$. This suspension is spun again 1 hour at 10,000 RPM and the clear supernatant fluid ($S_{60}$) is poured off. The precipitate is dissolved in water and saved for preparation of 14-3-2 protein of which about 90% is in the $P_{60}$ fraction. The $S_{60}$ solution is brought to 80% saturation by dissolving 143 g ammonium sulfate and 1.43 ml 1N NH$_4$OH in each liter of $S_{60}$. The suspension is spun 1 hour at 10,000 RPM and the clear supernatant fluid ($S_{80}$) is poured off. The $P_{80}$ residue is dissolved in water and saved for preparation of other brain proteins. The $S_{80}$ solution is brought to 100% saturation by dissolving 157 g ammonium sulfate in each liter of $S_{80}$. This solution is titrated to pH 4.0–4.2 with glacial acetic acid while being stirred rapidly. The suspension is immediately spun 1 hour at 10,000 RPM and the clear supernatant fluid is poured off and discarded. The precipitate (P 100) is suspended in a small volume of "Buffer A" continuing 0.5 mM EDTA, 5 mM 2-mercaptoethanol (about 200 ml for 12 brains starting material), adjusted to pH 7 with NaOH and then dialyzed overnight against 12 liters of the same buffer.

Anion exchange resin marketed under the trade designation "DE-52" is prepared by suspending the damp powder (25% solid) in ten volumes of 0.5M NaCl in 5 mM "Buffer A" and adjusting to pH 7.2 with 6N HCl. The "DE-52" is then washed several times with "Buffer A" by decantation and the slurry packed at 140 g/cm$^2$ pressure in a 2.5 cm glass chromatography column to a height of 20 to 25 cm. The column is washed overnight by pumping through at least 1 liter of "Buffer A". The dialyzed $P_{100}$ fraction is then pumped onto the column at a flow rate of 40–50 ml/hr and then the same wash buffer is pumped through at the same flow rate until most of the unbound protein is removed from the column. Following this, a NaCl and pH gradient is pumped through the column at a flow rate of 60–80 ml/hr with 10 ml fractions being taken. The gradient is made in a 9-chambered gradient device (Moore, B. W. et al. Chromatographic and electrophoretic fractionation of solulbe proteins of brain and liver J. Biol. Chem., 240, 1647, 1965). All buffers contain 0.5 mM EDTA and 5 mM 2-mer-captoethanol. The absorbances of the fractions are read at 280 nm and the large peak eluting at about 0.3–0.5M NaCl is located by checking the fractions for S-100 by immunodiffusion against anti-S-100 or by polyacrylamide gel electrophoresis. The fractions containing S-100 are pooled and enough solid ammonium sulfate is added to saturate the solution (750 mg ammonium sulfate per ml of solution). This solution is brought to pH 4.0–4.2 with glacial acetic acid while being stirred and immediately spun 30 min at 12,000 RPM. The supernatant fluid is poured off, the precipitate is dissolved in about 20–30 ml of water and this solution is adjusted to pH 7.2 with 1N NaOH.

A column of G-150 Sephadex is prepared (5×85 cm) and washed by pumping through buffer (0.5M potassium phosphate, 0.5 mM EDTA, 5 mM 2-mercaptoethanol, 0.01% NaN$_3$, pH 7.2) at a flow rate of about 40 ml/hr. The precipitated and dissolved S-100 from the "DE-52" step is pumped onto the G-150 column and eluted with the same buffer at the same rate. The major eluted peak of protein (read at 280 nm) contains S-100 at greater than 90% purity. Fractions containing S-100 are pooled and dialyzed against 0.05M potassium phosphate, 0.5 mM EDTA and 5 mM 2-mercaptoethanol, pH 7.2.

A column of A-50 DEAE Sephadex is prepared (2.5×15 cm) by equilibrating the ion exchanger with the same 0.05M buffer as above, and the dialyzed S-100 fraction from the G-150 column is pumped on at a flow rate of 40–50 ml/hr. The protein from the column is eluted with a linear gradient formed from a 2-chambered system consisting of 500 ml of the 0.05M potassium phosphate buffer, pH 7.2, and 500 ml 1M NaCl, 0.05M potassium phosphate, 0.05 mM EDTA, 5 mM 2-mercaptoethanol, pH 7.2. The S-100 emerges as a symmetrical peak which is desalted by passing through a 5×50 cm column of G-25 Sephadex equilibrated with water. The desalted S-100 is lyophilized and stored in a desiccator at −10° C. The yield from 4 kg of brains is 200–250 mg S-100.

INDUCTION OF SPECIFIC ANTISERA

Antisera was prepared by running the S-100 obtained from the above purification procedure on acrylamide gel electrophoresis (Moore, B. W. et al. Chromatographic and electrophoretic fractionation of soluble proteins of brain and liver, J. Biol. Chem. 240: 1647–1653, 1965), carefully excising the S-100 bands from several gels (Hartman et al. a Method for Immediate Visualization of Proteins in Acrylamide Gels and its use for Preparation of Antibodies to Enzymes, Anal. Biochem., 30: 39, 1969) and homogenizing the gel segments in complete Freund's adjuvant. Innoculations were made in rabbits (approximately 200 μg S-100) at multiple subcutaneous sites on the back at two week intervals until immuno-precipitation bands become visible against S-100 in double diffusion plates. When the specific antibody titer is greater than 2 mg/ml, the antiserum may be used in the radioimmunoassay. Antisera prepared against bovine S-100 or 14-3-2 have equivalent precipitation activity against their respective antigens from human brain or bovine brain and the use of antiserum directed against human antigens has not been required.

IODINATION OF HUMAN S-100

It was found essential to use $^{125}$I-human S-100 as the radiolabeled ligand in competition against unknown quantities of endogenous human S-100 in plasma. Although in precipitation reactions both appear to react equally, in a competitive binding situation, the homologous antigen has considerably higher affinity for the antibody. This fact markedly reduces the sensitivity of the radioimmunoassy if unlabeled heterologous antigen must compete for binding. Human S-100 was, therefore, purified for use in both the iodination reaction and for preparing standard curves. Though the methods used were identical to those used for bovine S-100 protein, preparations from human tissue are done with great care because of possible viral contamination. These procedures were thus carried out under reverse sterile techniques.

Higher specific activities are achieved using the lactoperoxidase method of iodination (Marchalonis, J. J., An enzymic method for the trace iodination of immunoglobulins and other proteins, Biochem. J., 113: 299, 1969; Morrison and Bayse, Catalysis of iodination by lactoperoxidase, Biochem., 9; 2995–3000, 1970; and Morrison et al., Use of lactoperoxidase catalyzed iodination in immunochemical studies, Immunochem., 8: 289, 1971) with modifications. The iodination mixture contained 5 μg human S-100 , 8.0×10$^{-3}$ Int. Units of Lactoperoxidase, 0.01 Int. units of glucose oxidase, 0.2 mg dextrose, and 1.00 mci of $^{125}$I as the iodide salt. The total volume was 85 μl with a final buffer concentration of 0.4M sodium acetate, pH 5.6. The glucose oxidase-dextrose comination provides a mild H$_2$O$_2$ generating system. After 1 hour incubation at room temperature, the reaction was stopped by the addition of 100 μl of 0.1M Na$_2$S$_2$O$_3$ and 100 1 of 0.1M NaI. Iodinated S-100 was separated from unreacted iodine by chromatography over Sephadex G-25 equilibrated with 0.1M phosphate buffer pH 7.5, 1% bovine serum albumin and 0.1% Triton X-100. S-100 iodinated in this way has a specific activity of approximately $10^5$ CPM/ng and is 80±5% immunoprecipitable by excess S-100.

RADIOIMMUNOASSAY PROCEDURE

Introduction

The assay requires the following data to be measured: (1) A standard competitive binding curve run in the presence of "standard plasma" which (a) contains no S-100, (b) has a well established and standarized quantity of intrinsic non-specific competitive binding, and (c) contains approximately the average degree of non-specific competitive binding found in the plasma samples under investigation: The CPM bound at the 0.0 ng/ml S-100 point in the standard curve, i.e., maximum blank of standard curve, Max Blank$_s$, is particularly important, (2) measurement of the counts per minute bound to the specific antibody by the unknown plasma (CPM$_u$) and (3) measurement of the counts per minute bound to the specific antibody by an unknown plasma after all S-100 has been removed without removing the proteins responsible for non-specific binding (Mas Blank$_u$). This last measurement permits an accurate evaluation of the degree to which non-specific competitive binding is interfering with the interaction between iodinated S-100 and the antibody in that particular sample, compared to the same property in the standard plasma. There is a definable relationship between the degree to which the non-specific binding proteins interfere with antibody binding to iodinated S-100 and their effect on endogenous S-100 binding in the same plasma sample.

Standard RIA Conditions

Each assay tube contained 200 μl of test plasma to which 100 μl of diluted (1:12,800, for example) anti S-100 antibody is added. The pH of the reaction is maintained at pH 6.7±0.0 by appropriate buffering. The reaction was allowed to proceed for 18 hours (overnight) at room temperature. After incubation, approximately 200,000 CPM of $^{125}$I-S-100 was added in 50 μl of buffer and an additional 2 hours incubation was carried out at room temperature. Following this incubation, 100 μl of diluted (1:80) normal rabbit serum is added (for Ig G carrier) followed by an additional 100 μl containing antirabbit IgG (50% in excess of equivalence). After an additional 2 hours incubation, the tubes were centrifuged and the supernatant removed. Following one wash with buffer, the tubes were counted. Under the above conditions, the CPM in the absence of anti-body (low blank) was approximately 1500 CPM (<1.0% total CPM added). Counts bound in the absence of unlabeled S-100 for the standard plasma (Max Blank$_s$) are approximately 40,000 CPM or 25% of the immunoreactive $^{125}$I-S-100 present in the tube. These conditions were determined empirically to be optimal for the sensitivity and range required for the test when carried out in plasma or serum.

Standard Curve

A standard curve is constructed by mixing of known quantities of purified S-100 (from procedure previously described) to standardized human plasma to produce the following final concentrations in ng/200 μl (volume of plasma assayed): 4.0, 3.0, 2.0, 1.5, 1.0, 0.5, 0.25, 0.0125 and 0.00. The standard plasma which acts as the medium for the reaction must have two properties: (1) It must have a level of non-specific binding interference which approximates that usually found in patient plasma; (2) It must contain no S-100. To satisfy the first criterion, 250 different randomly collected plasma samples were pooled. The second criterion was fulfilled by the following procedure for quantitatively removing low levels of S-100 without also removing the positively charged proteins responsible for non-specific competition.

Removal of S-100 from Plasma Without Altering Non-Specific Binding

S-100 protein has a high negative charge. The main source of binding interference comes from electrostatic interactions with positively charged endogenous plasma proteins. At pH 5.5, most plasma proteins with the exception of albumin and S-100 have a positive charge (those proteins with a positive charge at neutral pH have an even higher positive charge). When pH 5.5 plasma is exposed to DEAE-Sephadex A-50 (equilibrated at the same pH) only albumin and S-100 protein will bind to the gel. Potentially inhibitory proteins have no affinity for the positively charged matrix. S-100 with a molecular weight of about 20,000, however, can gain access to the interior of the gel beads whereas albumin cannot. The binding capacity for S-100, therefore, is many times that of albumin which immediately saturates only the exposed DEAE-residues. Thus, when plasma containing S-100 is incubated with DEAE-Sephadex, the S-100 is quantitatively removed by binding to the interior of the gel and the supernatant contains S-100 free plasma with non-specific binding properties unchanged.

S-100 free standard plasma was prepared from a large batch of pooled plasma with an average degree of interfering proteins by running the pooled plasma over a short DEAE column and collecting the eluent. The pH of the plasma was then returned to that required for assay and frozen for use in future standard curves. This standard plasma provides the uniform standard against which the non-specific binding properties of individual plasma samples can be measured.

Figure 1:
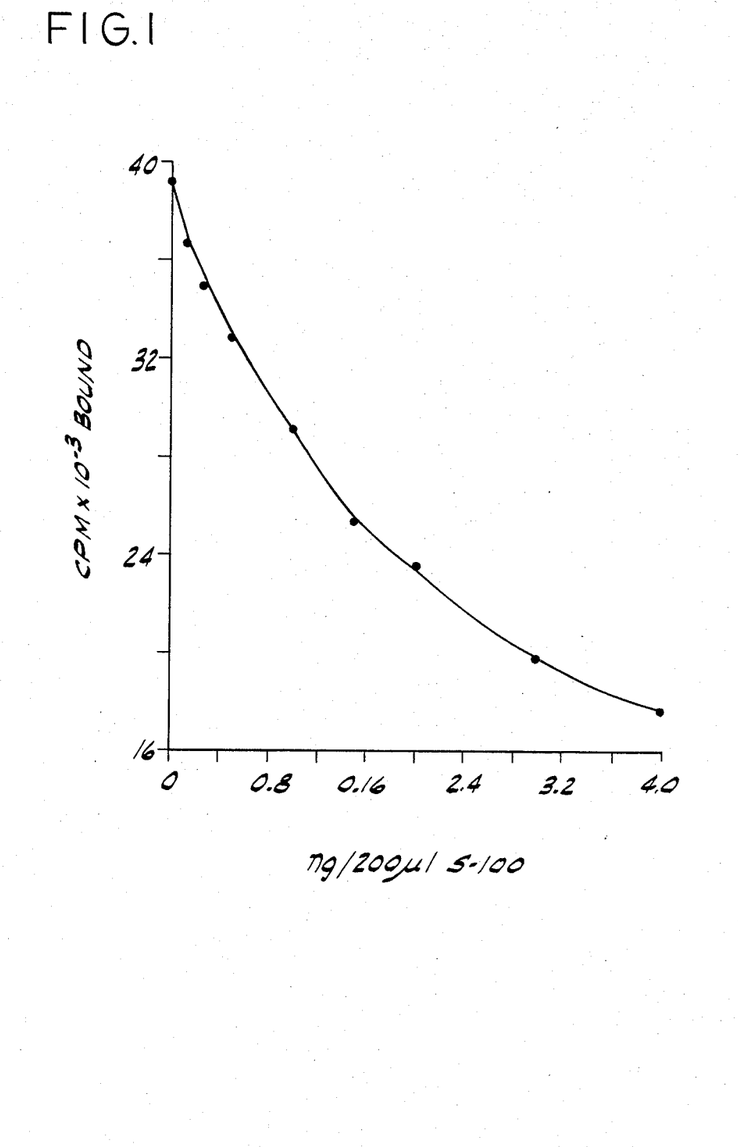
FIG. 1 is a graph depicting an illustrative standard curve for the protein S-100 obtained by plotting the amount of bound radioactively labeled S-100 against the concentration of standard solutions of S-100 expressed in terms of ng/200 $\mu$l S-100.

FIG. 1 shows an illustrative standard curve for the protein S-100 prepared using the standard plasma as a medium. The curve was obtained by plotting the amount of bound radioactively labeled S-100 against the concentration of standard solutions of S-100 expressed in terms of ng/200 μl S-100.

Measurement of Unknown Plasma Samples

In accordance with the present invention, two competitive binding assays are carried out on each unknown sample.

CPM$_u$: The first assay is the RIA measurement previously described and is carried out by running a 200 μl aliquot of the unknown plasma sample (in duplicate) through the standard RIA procedure described above to evaluate CPM bound in the presence of the unknown plasma (CPM$_u$).

Max Blank$_u$: The second assay consists in determining the CPM bound in the presence of the same unknown sample after adsorption of any endogenous S-100 as described. The removal is and must be accomplished without altering non-specific binding qualities of the plasma.

S-100 was removed from 500 μl of plasma by applying the method employed for preparing "standard plasma" on a smaller scale. The unknown plasma sample (pH adjusted to 5.5) was added to a tube containing 0.2 ml of packed DEAE-Sephadex A-50. After a 30 minute incubation at room temperature, the plasma was removed from the settled Sephadex and filtered through a glass wool plug in a Pasteur pipette. The pH was adjusted to 6.7±0.1 and duplicate 200 μl samples of this S-100 free plasma were run through the standard RIA as described. Radioactivity in the immunoprecipitate=Max blank$_u$. The volume changes that occur do not detectably alter non-specific binding.

Computation of NG/ML S-100 in Plasma

The following data are obtained from the above-described procedures:

1. Standard curve as in FIG. 1, described by ng/200 μl=$f_p$ (CPM).
2. Max blank$_s$=CPM bound at 0.0 ng in standard curve.
3. Max blank$_u$=CPM bound at 0.0 ng in unknown plasma.
4. (CPM$_u$)=CPM bound at unknown ng in same plasma.

Measurements 3 and 4 are carried out on each unknown sample.

Two intermediate values are obtained:

$$\Delta \text{ Max blank} = \text{Max blank}_s - \text{Max blank}_u$$

(value may by positive or negative)

$$Y = \text{fractional change in Max blank} = \frac{\Delta \text{ Max blank}}{\text{Max blank}_s}$$

Figure 2:
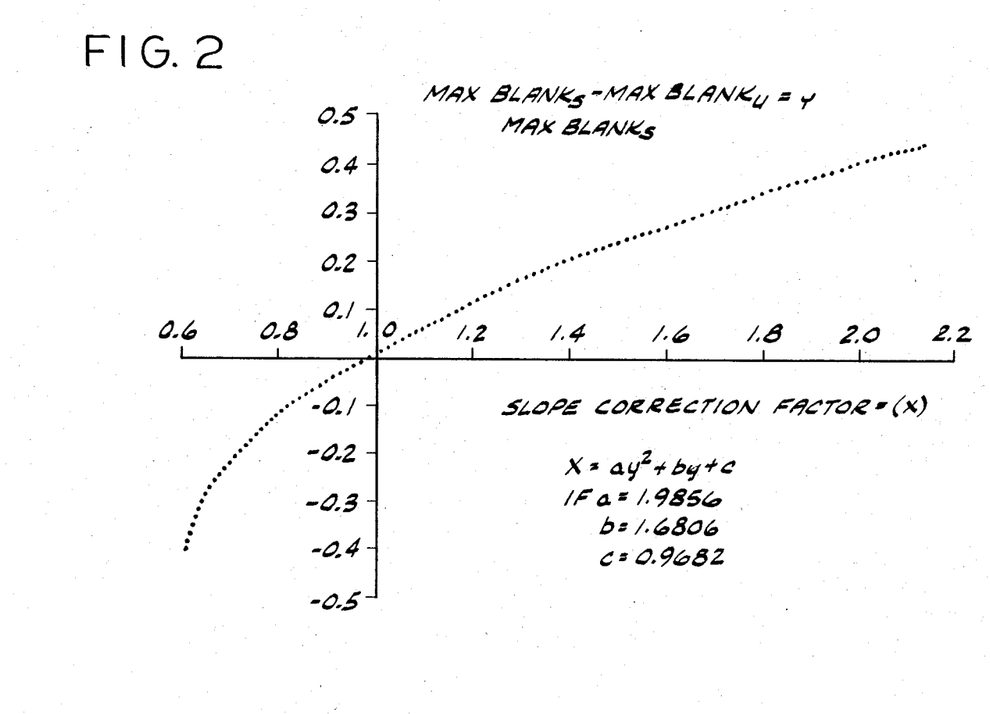
FIG. 2 is a graph depicting the relationship between the fractional change in Max blanks ($\Delta$ blank/Max blank$_s$) (Y) and the slope correction factor for an individual S-100 sample (X) in accordance with the practice of the invention.

The empirically derived relationship between the "fractional change in Max blank" (Y) and the "slope correction factor" (X) is shown in FIG. 2.

The following equation is used to compute ng/ml S-100 in the unknown sample:

$$ng/ml = 5Xf_p(\text{CPM}_u + \Delta\text{Max blank})$$

The computations made may be described in words as follows: (1) The difference between the Max blanks is added to the CPM bound by the unknown. This sum is converted to ng by reading from the standard curve or by computation using the polynominal function that describes the standard curve, $ng=f_p(CPM)$. (2) This answer which represents a first approximation of ng/200 μl is multiplied by the "slope correction factor" (X) which is read directly from FIG. 2 using (Y) or computed using the second order function describing that curve. (3) This answer in ng/200 μl is converted to ng/ml by multiplying by 5. These computations may be done, for example with a Wang mini computer program which utilizes CPM output on paper tape generated by the gamma counter.

Clinical Studies

Randomly collected plasma samples from 707 patients were tested using the above-described assay system. These samples had been previously tested using an assay system in which the degree of binding interference was not evaluated and no corrected S-100 level was made by means of the second assay described above for the radioimmunoassay method of the present invention. In these previous clinical tests, the 707 patients for which both clinical data and plasma S-100 levels were obtained were divided into (1) "Non-neurological Disorders", i.e. patients with no nervous system disorder mentioned in the hospital admission and/or discharge summary and (2) "Neurological Disorders", i.e. patients with any nervous system (including psychiatric) disorder, regardless of severity or whether a primary or secondary diagnosis. The results are shown in Table I.

TABLE I

PLASMA S-100 LEVELS COMPARISON OF TOTAL NON-NEUROLOGICAL VS. TOTAL NEUROLOGICAL PATIENTS[a]

| Diagnosis | No. | Mean S-100 ng/ml ± SEM | P |
|---|---|---|---|
| Total Non-neurological | 568 | 0.62 ± .06 | >0.001 |
| Total Neurological | 139 | 1.14 ± .16 | |

[a]Random collection of samples from hospitalized patients

The difference between these means is significant at p<0.001 using the Student's t-test. This comparison demonstrates that there is a clear statistical difference between plasma S-100 levels of the two populations.

"Nonneurological disorders" were subdivided into two categories: (1) Non-life threatening disorders (this group is very heterogeneous and included patients admitted for routine checkup and diagnostic evaluation, obstetrical patients, etc.) and (2) life-threatening disorders (including patients with malignancy, advanced diabetes, myocardial infarction, advanced liver or kidney disease, etc.). These categories are subjective; however, division of patients was made blind to S-100 levels. The results of the mean plasma S-100 levels of these groups are summarized in Table II.

TABLE II

PLASMA S-100 LEVELS COMPARISON OF DISEASE SEVERITY IN NON-NEUROLOGICAL[a] DISORDERS

| Diagnosis | No. | Mean S-100 ng/ml ± SEM | P |
|---|---|---|---|
| Non-Life Threatening | 233 | 0.56 ± .08 | NS |
| Life Threatening | 335 | 0.64 ± .08 | |

[a]Mean plasma levels of S-100 of the total neurological disorder sample was different (p 0.001) from either subgroup of non-neurological patients.

Although the mean level was slightly higher in the patients with life-threatening illness, the difference was not significant by t-test, indicating that the severity of non-neurological illness does not have an important effect on plasma S-100 levels. The total neurological group was different from both subgroups of non-neurological subgroups (p<0.001).

Neurological disorders were subdivided into the following categories: (1) "Acute Neurological", i.e., disorders in which the plasma sample was obtained within one week of the onset of an acute primary neurological problem (e.g., stroke, intracranial bleed, head injury, seizure, etc.) or during the course of a progressive neurological problem (e.g., brain tumor, exacerbation of multiple sclerosis, etc.); (2) "Dementia", i.e., patients whose primary diagnosis was dementia; (3) "Chronic Neurological", i.e., patients with a primary diagnosis of neurological disorder but in which no apparent progression was occuring (e.g., remote strokes, non-progressive M.S., etc.); (4) "Parkinson's Disease"; (5) "Peripheral Neurological" disorders when primary (e.g., herniated lumbar vertebral disc); and (6) "Incidental Neurological and Psychiatric", i.e., patients who had an incidental diagnosis of a neurological problem (e.g., diabetic renal disease with complications including diabetic neuropathy) or patients with a psychiatric diagnosis including alcohol abuse.

Statistical comparisons between the diagnostic subgroups are shown in Table III and demonstrate several important points.

TABLE III
PLASMA S-100 LEVELS COMPARISON OF SUBGROUPS OF NEUROLOGICAL PATIENTS VS. TOTAL NON-NEUROLOGICAL PATIENTS

| Diagnosis | No. | Mean S-100 ng/ml ± SEM | | $P<$ |
|---|---|---|---|---|
| Total Non-Neuro. | (568) | 0.62 | ± .06 | |
| Acute Neuro. | (47) | 1.82 | .40 | $P<.001$ |
| Dementia | (6) | 2.36 | .78 | $P<.001$ |
| Chronic Neuro. | (23) | 0.48 | .24 | NS |
| Peripheral Neuro. | (23) | 0.72 | .34 | NS |
| Parkinson's Disease | (7) | 0.52 | .34 | NS |
| Incidental & Psychiatric | (33) | 0.84 | .26 | NS |

Two neurological categories had highly significant increases in plasma S-100 levels, acute primary neurological disorders and dementia. The importance of the presence of an active neurological process for the finding of elevated plasma S-100 levels was consistent with the preliminary clinical studies and the rapid biological clearance of the small protein from the blood.

The presence of S-100 in the plasma of patients with a primary diagnosis of dementia may indicate that alterations in glial cells is actively occurring in this group of patients. The other neurological groups were not significantly different from the control populations. However, in the psychiatric group there were six patients with an S-100 level greater than 2.0 ng/ml. All these patients had a diagnosis of alcoholism. This observation is again suggestive of either glial damage or alteration in glial membranes, permitting loss of S-100 in this disorder.

When patients were divided on the basis of sex, no significant differences in plasma S-100 levels were observed in either neurological or non-neurological groups. These results are shown in Table IV and indicate a lack of bias in the test based on sex.

TABLE IV
PLASMA S-100 LEVELS COMPARISON OF LEVELS IN MALES VS. FEMALES IN THE TWO BASIC CATEGORIES

| Diagnosis | No. | | Mean S-100 .ng/ml ± SEM | P |
|---|---|---|---|---|
| Total Neurological | Male | (57) | 0.90 ± .20 | NS |
| | Female | (82) | 1.32 ± .26 | |
| Total Non-Neuro. | Male | (198) | 0.68 ± .10 | NS |
| | Female | (370) | 0.58 ± .08 | |

When patients were divided on the basis of age, no difference was observed in mean S-100 plasma levels in the non-neurological diagnostic category. However, acute neurological patients older than 40 had significantly higher S-100 levels ($p<0.02$) than those whose age was less than 40. This was due to the greater severity of neurological disorders in the older group. These results are shown in Table V.

TABLE V
PLASMA S-100 LEVELS INFLUENCE OF AGE ON S-100 LEVELS

| Diagnosis | Age | No. | Mean S-100 ng/ml ± SEM | P |
|---|---|---|---|---|
| Total Non-Neuro | 0.40- | (127) | 0.64 ± .12 | NS |
| | 40-UP[a] | (434) | 0060 ± .10 | |
| Acute Neuro. | 0-40 | (6) | 0.66 ± .08 | .02 |
| | 40-UP[b] | (41) | 2.02 ± .44 | |

[a]Older patients in this category had more severe illness but since the diseases are Non-neurological this fact does not affect S-100 levels.
[b]Older patients in this category had more severe neurological illness.

A further comparison is seen on the basis of age in Table VI where acute neurological patients are compared with non-neurological patients in different age groups. The largest differences are seen in the 40–60 and 60-up groups. This difference again reflects the greater severity of acute neurological disorders in the higher age groups rather than a bias on the basis of age per se, as indicated by the lack of significant differences in non-neurological groups on the basis of age.

TABLE VI
PLASMA S-100 LEVELS EFFECT OF AGE ON DIFFERENCES IN S-100 LEVELS OF NEUROLOGICAL AND NON-NEUROLOGICAL PATIENTS

| Diagnosis | Age | No. | Mean S-100 ng/ml ± SEM | P |
|---|---|---|---|---|
| Acute Neuro. | 0–20 | 0 | | |
| Non-Neuro. | 0–20 | 20 | .60 ± .24 | |
| Acute Neuro. | 20–40 | 6 | 0.66 ± .08 | NS |
| Non-Neuro. | 20–40 | 107 | 0.64 ± .12 | |
| Acute Neuro. | 40–60[a] | 11 | 3.18 ± 1.26 | $>>.001$ |
| Non-Neuro. | 40–60 | 181 | 0.40 ± .08 | |
| Acute Neuro. | 60–UP[a] | 30 | 1.60 ± .38 | .02 |
| Non-Neuro. | 60–UP | 253 | 0.76 ± .10 | |

[a]Patients in the older age groups had more severe neurological disorders - older patients in the non-neurological group also had more severe illness but this fact does not reflect in altered S-100 levels.

The plasma samples obtained in the above-reported studies were retested using the radioimmunoassay method of the present invention and shown to correlate well on an individual basis with severity and acuteness of the neurological disorder. However, with the method of the present invention, it is possible to more accurately estimate the concentration of an antigen such as S-100 in the presence of variable and unknown quantities of non-specific binding interference.

In using the method of the present invention, apparent false positives were reduced to 10% between 1.5 ng and 2.5 S-100 ng/ml, 5% levels between 2.5 and 3.5 ng/ml and 0% at levels greater than 3.5 ng/ml.

The presence of S-100 in plasma is of limited value in the differential diagnosis of destructive neurological disorders since all such diseases may lead to elevated plasma levels. However, because the S-100 protein is cleared rapidly, it offers an objective means of evaluating, on a day to day basis, the course of the disease and the effectiveness of treatment in altering the course. This renders the present invention particularly useful in the treatment of multiple sclerosis and other demyelinating diseases.

The following tabulation shows the results obtained in carrying out the method of the invention on plasma samples for 25 patients with active and inactive multiple sclerosis (MS).

| RANK ORDER COMPARISON OF S-100 LEVELS IN PATIENTS WITH ACTIVE MS AND INACTIVE MS | | |
|---|---|---|
| RANK ORDER | [1]DEFINITE ACTIVE MS ng/ml | [2]DIFINITE INACTIVE MS ng/ml |
| 1 | 3.96 | |
| 2 | 3.82 | |
| 3 | 3.50 | |
| 4 | 3.50 | |
| 5 | 3.46 | |
| 6 | | 3.34 |
| 7 | 3.16 | |
| 8 | 3.08 | |
| 9 | | 2.98 on steroids |
| 10 | 2.60 | |
| 11 | 2.46 | |
| 12 | | 2.18 |
| 13 | 2.14 | |
| 14 | | 1.78 |
| 15 | | 1.54 |
| 16 | | 1.42 |
| 17 | | 1.02 |
| 18 | | .92 |
| 19 | | .78 on steroids |
| 20 | | .74 |
| 21 | | .74 |
| 22 | | .68 |
| 23 | | .48 |
| 24 | | .28 |
| 25 | | .22 |
| | n = 10 | n = 15 |
| | X ± SEM = 3.16 ± .20 | X ± SEM = 1.28 ± .26 |
| | t = 18.56 | |
| | p 0.001 | |

[1]Definite Active MS = Definite diagnosis of Multiple Sclerosis. Clear clinical exacerbation within 1 week of obtaining sample.
[2]Definite Inactive MS = Definite diagnosis of Multiple Sclerosis. No clear clinical change within 1 week of obtaining sample.

Figure 3:
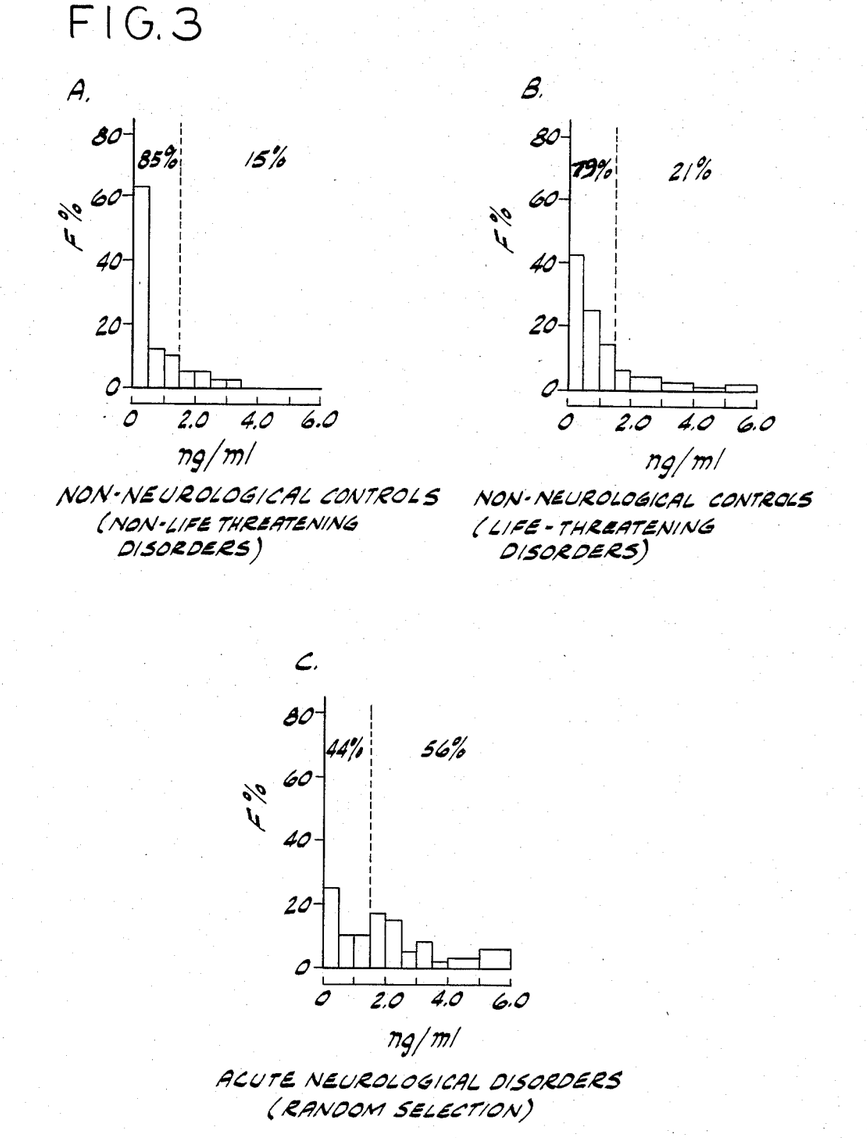
FIG. 3 shows three frequency distribution histograms (designated A, B and C) expressed as frequency of occurrence (%) vs. measured S-100 plasma levels determined in accordance with the practice of the invention.

FIG. 3 shows an analysis of the frequency distribution histograms for the two control groups and the acute neurological patients whose plasma was tested according to the method of the invention. The first histogram (FIG. 3A) shows the distribution of levels in the least ill non-neurological control group (i.e., patients who did not have life-threatening illness). Eighty-five percent of these patients had S-100 plasma levels less than 1.5 ng/ml (i.e., 15% had levels greater than this value). 10% had levels greater than 2.0 ng/ml, 2% had levels greater than 3.0 ng/ml and no patients (0%) had levels greater than 3.5 ng/ml. In the severely ill control group (FIG. 3B), 8% of the patients had levels above 3.5 ng/ml. These patients had either: (1) severely compromised renal function or (2) disseminated carcinomatosis. If patients with these two illnesses are removed from the sample, the two control histograms become essentially indistinguishable. During renal failure, clearance of S-100 by the kidney is diminished, resulting in an increase of S-100 blood levels. In the presence of disseminated carcinoma, increases in S-100 blood levels may be explained by CNS involvement not mentioned in the patient chart. In either case, no serious problem in interpretation occurs in distinguishing these disorders from neurological problems through the practice of the method of the invention.

Control histograms (FIGS. 3A and 3B) are in many ways more important than that for the neurological disorders (FIG. 3C). The control distribution establishes the upper limits and the frequency of occurrence for specific levels in controls (i.e., non-neurological patients). Control plasmas should therefore be measured with each assay and the larger the control data base, the greater the precision by which a patient can be classified as "non-control", i.e., either "neurological" or one of the two above-noted exclusions.

FIG. 3C shows the results of frequency distribution analysis in patients with acute neurological disorders using data obtained through the assay of the present invention. Fifty-six percent of the patients had levels greater than 1.5 ng/ml compared to 15% of non-neurological patients (excluding renal shutdown and disseminated carcinomatosis). In contrast, with the prior assay for which results were presented above, only 41% of acute neurological patients had levels 1.5 ng/ml. This improvement in accuracy and sensitivity is attributable to the radioimmunoassay of this invention. More important than the percentages are the particular types of disorders which have high or low levels. The group with levels below 1.5 ng/ml contained patients with the least severe or more remote disorders. For example, the most common diagnosis in this category was a stroke that had occurred more than three days prior to drawing the patient sample. Two other groups were highly represented in the low level category: (1) seizure disorder, and (2) rule/out MS, stroke and brain tumor (about an equal number of "rule outs" were in the high level categories). The remainder of the patients in the below 1.5 ng/ml category were isolated diagnoses but none were compatible with both acute and major destructive lesions. Thus, this segment of the patient population were not viewed as "false negatives" since as far as could be determined, these patients should have shown low levels and the assay is, in fact, providing a correct evaluation of their current clinical state.

The patients with levels between 1.5 and 4.0 ng/ml (42% of this patient sample had a wide variety of diagnoses, including stroke, MS, meningitis, metastatic carcinoma, low grade astrocytoma and undiagnosed active neurological disorder ("rule out" MS, brain tumor, etc.). Three patients probably should have fallen into the low level group, one with a small stroke 6 days post-occurrence, and 2 with seizure disorders. These could be considered "false positives". The five remaining patients had levels greater than 4 ng/ml. They consisted of three brain tumors (two metastatic, one glioblastoma multiforme) and two recent strokes. One stroke that had occurred on the day of admission had a level of 12.8 ng/ml and the glioblastoma had a level of 62 ng/ml (required a 1:4 dilution to be measured). The samples represented were drawn randomly from a whole hospital population.

A clinical study was conducted on 57 neurological intensive care unit (ICU) patients to determine the sensitivity and reliability of S-100 level determinations in such a group of easily evaluated patients, most of whom had CT (computed tomography) scans run. In this study, the initial clinical evaluation (C1) and the final clinical evaluation (CF) were done blind to the S-100 levels based upon the symptology involved by two independent physicians. The S-100 levels were determined blind to the clinical picture or evaluation. The CT scans were not done blindly but with the clinical picture or evaluation available.

The results are set forth in the following tables which also include conclusions drawn from the amount of deficit (D) at the time of discharge in the light of the three modes of evaluation, i.e. admission clinical, CT Scan and S-100 levels:

| Patient | Diagnosis | Cl D | CF D | CF-Cl Days | CT D | S-100 D | S-Cl Days | S-100 NG/ML VAL 1 | VAL 2 | VAL 3 | VAL 4 | Remarks |
|---|---|---|---|---|---|---|---|---|---|---|---|---|
| 1 | CVA | 4 | 4 | 4 | 4 | 4 | 3 | 9.8 | | | | Died |
| 2 | CVA | 4 | 4 | 21 | 4 | 4 | 3 | 8.7 | 9.0 | 2.1 | | |
| 3 | HEMORR. | 4 | 4 | 5 | 4 | 4 | 3 | 7.3 | 6.7 | | | Died |
| 4 | HEMORR. | 4 | 4 | 1 | 4 | 4 | 1 | 8.3 | | | | Died |
| 5 | CVA | 4 | 4 | 30 | 3 | 4 | 5 | 10.3 | 12.5 | 13.1 | | |
| 6 | CVA | 2 | 3 | 50 | 0 | 3 | 2 | 2.5 | 4.2 | 6.0 | 1.8 | CT Op. Time |
| 7 | EMBOLISM | 3 | 3 | 18 | 3 | 3 | 1 | 2.0 | 4.9 | 3.1 | | |
| 8 | CVA | 3 | 2 | 21 | 2 | 3 | 4 | 4.2 | 6.0 | 3.8 | | |
| 9 | CB HEMAN | 3 | 3 | 30 | 3 | 3 | 4 | 4.4 | 4.9 | 2.1 | | |
| 10 | CVA | 2 | 3 | 40 | 0 | 3 | 3 | 2.3 | 2.6 | 4.0 | | CT Op. Time |
| 11 | HEMORR. | 2 | 2 | 5 | 2 | 3 | 1 | 6.7 | 2.3 | 3.8 | | |
| 12 | CVA | 2 | 2 | 44 | 3 | 2 | 2 | 3.0 | 4.3 | 3.8 | | |
| 13 | VERTIGO | 2 | 1 | 8 | 0 | 2 | 1 | 4.1 | 1.1 | 1.3 | | CT Und. Est. |
| 14 | CVA | 2 | 2 | 16 | 0 | 2 | 1 | 0.6 | 4.6 | 1.6 | 1.0 | |
| 15 | TIA | 0 | 0 | 6 | 0 | 2 | 2 | 4.6 | 2.9 | 2.2 | | |
| 16 | HEMORR.1 | 2 | 3 | 53 | 3 | 2 | 1 | 3.2 | 1.6 | 0.0 | | |
| | HEMMOR.2 | | | | 0 | 2 | 2 | 1.5 | 2.9 | | | |
| 17 | CVA | 2 | 2 | 27 | 2 | 2 | 3 | 2.9 | 2.9 | 1.4 | | |
| 18 | CVA(1) | 2 | 2 | 63 | 0 | 1 | 1 | 2.9 | 2.7 | 2.4 | | CT Und. Est. |
| | CVA(2) | 2 | 2 | 19 | 0 | 2 | 1 | 1.0 | 2.7 | 3.2 | | CT Und. Est. |
| 19 | CVA | 2 | 0 | 13 | 0 | 2 | 1 | 2.1 | 2.8 | 3.8 | 1.4 | CT Und. Est. |
| 20 | TRAUMA | 1 | 0 | 4 | 1 | 1 | 2 | 3.0 | 1.0 | | | |
| 21 | CVA | 2 | 1 | 12 | 0 | 1 | 3 | 1.7 | 3.4 | 1.4 | | |
| 22 | CVA | 2 | 1 | 13 | 0 | 1 | 2 | 2.0 | 1.5 | 2.2 | | |
| 23 | CB.DISOR | 1 | 1 | 4 | 0 | 1 | 3 | 1.6 | | | | |
| 24 | CVA | 1 | 2 | 5 | 0 | 1 | 1 | 1.7 | 2.8 | 1.7 | | CT Und. Est. |
| 25 | HEMORR. | 1 | 1 | 7 | 3 | 1 | 4 | 0.9 | 0.4 | 2.4 | | CT Und. Est. |
| 26 | DEMENTIA | 1 | 1 | 72 | 1 | 1 | 0 | 1.8 | 1.3 | 0.8 | 1.9 | |
| 27 | CVA | 1 | 1 | 27 | 0 | 1 | 1 | 2.1 | 1.7 | | | CT Und. Est. |
| 28 | PARATHES | 0 | 0 | 14 | 0 | 1 | 3 | 1.2 | 2.1 | 0.6 | | Prob. MS |
| 29 | CVA | 2 | 1 | 20 | 2 | 1 | 2 | 1.0 | 1.8 | 0.8 | | |
| 30 | CVA | 2 | 1 | 7 | 0 | 1 | 3 | 2.0 | 0.9 | | | CT Und. Est. |
| 31 | TIA | 1 | 0 | 5 | 0 | 1 | 1 | 1.2 | 1.6 | 0.2 | 32 | CVA |
| 32 | CVA | 1 | 6 | 0 | 1 | 2 | 0.8 | 1.6 | | | | CT Und. Est. |
| 33 | CVA | 2 | 1 | 5 | 0 | 1 | 1 | 1.2 | 1.8 | 1.5 | | |
| 34 | RAD. MYEL | 0 | 1 | 2 | 0 | 1 | 4 | 1.4 | 2.9 | 2.3 | | |
| 35 | CVA | 1 | 1 | 29 | 0 | 1 | 9 | 1.9 | 2.1 | | | |
| 36 | CVA | 2 | 1 | 29 | | 1 | 2 | 1.9 | 1.2 | 0.3 | 0.5 | |
| 37 | HEMIPARE | 3 | 2 | 6 | 0 | 1 | 1 | 0.7 | 0.7 | 1.6 | | R/O Ms |
| 38 | I.C. CVA | 3 | 1 | 9 | 2 | 1 | 4 | 0.0 | 0.9 | 1.8 | | Sml Lesion |
| 39 | HYPOTENS | 0 | 0 | 32 | 0 | 1 | 0 | 1.5 | 1.3 | 0.9 | | |
| 40 | LABRYNIT | 0 | 0 | 3 | | 1 | 1 | 1.8 | | | | |
| 41 | SEPSIS | 3 | 0 | 30 | 0 | 0 | 1 | 1.4 | 1.1 | | | |
| 42 | MIGRAINE | 1 | 0 | 2 | 0 | 0 | 2 | 0.8 | | | | |
| 43 | INCR. MAS | 2 | 1 | 88 | 1 | 0 | 3 | 0.9 | 1.1 | 0.4 | | |
| 44 | CATARACT | 0 | 0 | 5 | | 0 | 1 | 0.9 | 0.3 | 0.8 | | |
| 45 | I.C. CVA | 2 | 2 | 10 | 1 | 0 | 1 | 0.2 | 0.9 | 0.4 | | Sml Lesion |
| 46 | SEIZURE | 2 | 0 | 8 | 0 | 0 | 2 | 0.9 | | | | |
| 47 | BELL PAL | 2 | 1 | 54 | 0 | 0 | 3 | 0.4 | 0.8 | | | Sml Lesion |
| 48 | PSYCHOSI | U | 0 | 32 | | 0 | 14 | 0.8 | | | | |
| 49 | TIA | 1 | 0 | 5 | 0 | 0 | 2 | 1.1 | 0.3 | | | |
| 50 | MS | 2 | 0 | 0 | | 0 | 1 | 0.8 | 1.0 | 1.2 | | |
| 51 | PARKINSO | 3 | 0 | 9 | 3 | 0 | 4 | 0.1 | 0.8 | 0.7 | | CT Error |
| 52 | TIA | 2 | 0 | 14 | 0 | 0 | 1 | 0.1 | 0.7 | 0.0 | | |
| 53 | CVA | 2 | 1 | 18 | 1 | 0 | 3 | 0.3 | | | | |
| 54 | CVA | 2 | 1 | 4 | 0 | 0 | 2 | 0.2 | 0.9 | | | |
| 55 | DIPLOPIA | 1 | 0 | 8 | 0 | 0 | 4 | 0.2 | 0.0 | 0.0 | | Sm. Eye Hem |
| 56 | CVA | 3 | 1 | 20 | 0 | 0 | 3 | 0.0 | 0.0 | 0.0 | | |
| 57 | MI | U | 0 | 2 | | 0 | 2 | 0.3 | | | | Mi Not CVA |

Key:
D = Amount of Deficit
Cl = Initial Clinical
CF = Final Clinical
CL = CT Scan
CF-Cl = Days between final clinical and initial clinical
S-Cl = Days between patient admission and first S-100 Determination
Val 2 = 2 days after Val 1, Val 3 = 2 days after Val 2, etc.
CVA = cerebral vascular accident (stroke)
CB Heman = blood vessel tumor of cerebellum
TIA = transient ischemic attack
Trauma = head trauma
Parathes = weaknesses
Rad. Myel = Radiation myelitis
Hemipare = paralysis on one side
Labrynit = vertigo
MI = myocardial infarction
MS = multiple sclerosis

| Scale: | For Determining Amount of Deficit |
|---|---|

-continued

4 = Massive Lesion

-continued

```
            Multiple Systems Involved
            Motor: Sensory: Mental: Autonomic
      3 =   Very Large Lesion
            2 Systems with Major Involvement
            1 System Massively Involved
      2 =   Significant Lesion
            1 or More Systems
      1 =   Small Lesion
            1 System Only
      0 =   No Lesion
            No Clinical Change
```

DEFICIT AT DISCHARGE = 4
(Massive - More Than Two Systems)
Predictions of Deficit
(+) = Overestimate (C) = Correct (−) Underestimate (Miss) = Underestimate

|  | ADMISSION CLINICAL | | | CT SCAN | | | S-100 SERIES | | |
|---|---|---|---|---|---|---|---|---|---|
|  | C | (−) | Miss | C | (−) | Miss | C | (−) | Miss |
| N = 5 | 5 | 0 | 0 | 5 | 1 | 0 | 5 | 0 | 0 |
| Fraction | DETECTED 5/5 | MISS 0/5 | | DETECTED 5/5 | MISS 0/5 | | DETECTED 5/5 | MISS 0/5 | |

Conclusion: All modes correctly evaluate massive lesions

DEFICIT AT DISCHARGE = 3
(Major Involvement of Two Systems)

|  | ADMISSION CLINICAL | | | CT-SCAN | | | S-100 SERIES | | |
|---|---|---|---|---|---|---|---|---|---|
|  | (+) | C | (−) MISS | (+) | C | (−) MISS | (+) | C | (−) Miss |
| N = 5 | 0 | 2 | 3   0 | 0 | 3 | 0   2 | 0 | 4 | 1   0 |
| FRACTION | DETECTED 5/5 | MISS 0/5 | | DETECTED 3/5 | MISS 2/5 | | DETECTED 5/5 | MISS 0/5 | |

Conclusion: CT-scan can miss major new lesions when complicated by the presence of other CNS pathology.
S-100 levels are not influenced by previous CNS pathology.

DEFICIT AT DISCHARGE = 2
(Major Involvement of One System or Significant Involvement of 2 Systems)

|  | ADMISSION CLINICAL | | | CT-SCAN | | | S-100 SERIES | | |
|---|---|---|---|---|---|---|---|---|---|
|  | (+) | C | (−) MISS | (+) | C | (−) MISS | (+) | C | (−) MISS |
| N = 10 | 2 | 7 | 1   0 | 2 | 2 | 1   5 | 2 | 5 | 2   1 |
| FRACTION | DETECTED 10/10 | MISS 0/7 | | DETECTED 5/10 | MISS 5/10 | | DETECTED 9/10 | MISS 1/10 | |

Conclusion: CT-scan misses half of lesions of this size.
Frequently run on admission to rule out hemorrhage or complicated by previous CNS lesion.
There is no significant lag time before S-100 appears.
Lesions of this size detected by S-100 test. Over or under estimates due mainly to lesion site.

DEFICIT AT DISCHARGE = 1
(Small But Definite Deficit)

|  | ADMISSION CLINICAL | | | CT-SCAN | | | S-100 SERIES | | |
|---|---|---|---|---|---|---|---|---|---|
|  | (+) | C | MISS | (+) | C | MISS | (+) | C | MISS |
| M = 20 | 14 | 5 | 1 | 3 | 3 | 14 | 1 | 14 | 5 |
| FRACTION | DETECTED 19/20 | MISS 1/20 | | DETECTED 6/20 | MISS 14/20 | | DETECTED 15/20 | MISS 5/20 | |

Conclusion: Most lesions of this size are not detected by CT-scan.
Clinically at admission these lesions appear worse than, in fact, they are.
The S-100 test is a better predictor than either the admission clinical picture or the CT-scan for these lesions; but may be negative if the lesion is small and in a sensitive site or drawn too late.

DEFICIT AT DISCHARGE = 0)
(No Clinically Detectable Deficit)

|  | ADMISSION CLINICAL | | | S-100 SERIES | | |
|---|---|---|---|---|---|---|
|  | (+2) | (+1) | C | (+2) | (+1) | C |
| N = 18 | 6 | 5 | 7 | 2 | 5 | 11 |
| FRACTION | OVEREST 11/18 | RECT 7/18 | OVEREST 7/18 | CORRECT 11/18 | | |

Conclusion: There may be substantial clinically silent lesions in patients which may be detectable by S-100 blood levels.

It can be seen that the determination of S-100 blood levels in accordance with the present invention represents the more sensitive and reliable test for determining acute neurological damage and more accurately predicts the deficit at discharge than the admission clinical impression which tends to greatly overestimate the deficit or the CT scan which tends to greatly underestimate significant and small lesions. The S-100 level determinations also enables one to detect some damage in patients who completely recover indicating that they may have ischemic damage and not benign TIA.

The following table shows the normal S-100 levels as determined in a large number of non-neurological patients:

| NORMAL S-100 LEVELS |
|---|
| RANDOM CONTROLS DONE FOR QUALITY CONTROL DURING STUDY (NON-NEUROLOGICAL) |
| N = 26     Mean = 0.82 ng ml |
|            SD = 0.46 |
|            Maximum value = 1.8 ng/ml |
| RANDOM CONTROLS IN ORIGINAL STUDY WITHOUT BASELINE CORRECTIONS (Non-Neurological) |
| N = 568    Mean = 0.62 ng ml |
|            SD = 1.42 ng ml |

Based on the foregoing, the radioimmunoassay method of the present invention has the advantages of being noninvasive and relatively inexpensive and of providing a current estimate of the progress of destructive lesions which is not complicated by previous disorders. It also involves no significant lag time and provides a relatively straight forward interpretation for the clinician. It does not, however, provide information on the lesion site, differentiate between causes of destruction or pick up previous lesions.

In view of the above, it will be seen that the several objects of the invention are achieved and other advantageous results attained.

As various changes could be made in the above methods without departing from the scope of the invention, it is intended that all matter contained in the above description and shown in the accompanying drawings shall be interpreted as illustrative and not in a limiting sense.

What is claimed is:

1. A radioimmunoassay method for the in vitro determination of the protein S-100 from an unknown test blood sample which comprises the steps of:

(a) preparing a standard blood formulation containing substantially no S-100 and approximately the average degree of non-specific competitive binding found in the unknown test blood sample;

(b) mixing known quantities of S-100 in purified form with said standard blood formulation to provide a reference standard;

(c) mixing said unknown test blood sample with a radioactively labeled sample of S-100 and an antibody capable of immunoreactivity with S-100;

(d) incubating the last resultant mixture to produce antibody bound radioactively labeled S-100 and unbound radioactively labeled S-100;
(e) separating the antibody bound S-100 from the unbound S-100;
(f) determining the relative amounts of antibody bound radioactively labeled S-100 and unbound radioactively labeled S-100;
(g) separately repeating steps (c), (d), (e) and (f) with an unknown test blood sample from which S-100 has been substantially removed; and
(h) determining the amount of S-100 from said reference standard and the determinations made in steps (f) and (g).

2. A radioimmunoassay method as set forth in claim 1 wherein said unknown test blood sample is plasma.

3. A radioimmunoassay method as set forth in claim 1 wherein the amount of S-100 determined is between 0.20 and 20.0 ng/ml of plasma.

4. A radioimmunoassay method as set forth in claim 1 wherein the antibody in step (c) is specific for S-100.

5. A radioimmunoassay method as set forth in claim 1 wherein S-100 is removed from the unknown test blood sample used in step (g) by being bound to a positively charged material which binds only S-100 and albumin.

6. A radioimmunoassay method for the in vitro determination from an unknown test blood sample of the normal soluble endogenous cytoplasmic protein 14-3-2 released into the blood in the course of neurological diseases and which is susceptible to separation from other proteins simultaneously released into the blood which method comprises the steps of:
(a) preparing a standard blood formulation containing substantially none of the said protein and approximately the average degree of non-specific competitive binding found in the unknown test blood sample;
(b) mixing known quantities of said protein in purified form with said standard blood formulation to provide a reference standard;
(c) mixing said unknown test blood sample with a radioactively labeled sample of said protein and an antibody capable of immunoreactivity with said protein;
(d) incubating the last resultant mixture to produce antibody bound radioactively labeled protein and unbound radioactively labeled protein;
(e) separating the antibody bound protein from the unbound protein;
(f) determining the relative amounts of antibody bound radioactively labeled protein and unbound radioactively labeled protein;
(g) separately repeating steps (c), (d), (e) and (f) with an unknown test blood sample from which said protein has been substantially removed; and
(h) determining the amount of said protein from said reference standard and the determinations made in steps (f) and (g).

* * * * *